United States Patent
Doerr et al.

(10) Patent No.: US 9,339,644 B2
(45) Date of Patent: May 17, 2016

(54) APPARATUS FOR MEDICAL APPLICATIONS (75) Inventors: Thomas Doerr, Berlin (DE); Ingo Weiss, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 1358 days.

(21) Appl. No.: 13/004,165

(22) Filed: Jan. 11, 2011

(65) Prior Publication Data
US 2011/0172756 A1  Jul. 14, 2011

Related U.S. Application Data (60) Provisional application No. 61/294,864, filed on Jan. 14, 2010.

(51) Int. Cl.
  *A61N 1/05* (2006.01)
  *A61N 1/08* (2006.01)
  *G01R 33/28* (2006.01)

(52) U.S. Cl.
  CPC ............. *A61N 1/05* (2013.01); *A61N 2001/086* (2013.01); *G01R 33/288* (2013.01)

(58) Field of Classification Search
  None
  See application file for complete search history.

(56) References Cited

U.S. PATENT DOCUMENTS

| | | | | |
|---|---|---|---|---|
| 4,744,359 | A * | 5/1988 | Hatta | A61B 18/08 219/497 |
| 7,285,118 | B1 * | 10/2007 | Lozano | 606/41 |
| 2001/0053882 | A1 * | 12/2001 | Haddock et al. | 600/549 |
| 2005/0222658 | A1 * | 10/2005 | Hoegh et al. | 607/116 |
| 2006/0111706 | A1 | 5/2006 | Truckai et al. | |
| 2006/0116747 | A1 * | 6/2006 | Eick et al. | 607/122 |
| 2008/0208180 | A1 * | 8/2008 | Cartier | A61B 18/24 606/15 |
| 2008/0221568 | A1 | 9/2008 | Stone | |
| 2008/0319519 | A1 * | 12/2008 | Magers | 607/106 |

OTHER PUBLICATIONS

European Search Report and Notes to the European Search Report on European Patent Application No. EP 11 15 0326, dated May 13, 2011 (6 pages).

* cited by examiner

*Primary Examiner* — Brian T Gedeon
*Assistant Examiner* — Ankit Tejani
(74) *Attorney, Agent, or Firm* — Buchanan Ingersoll & Rooney PC

(57) ABSTRACT

The present invention relates to an apparatus for medical applications. The apparatus includes an oblong conductive element having a distal end. A resistance element is disposed in the vicinity of the distal end. The resistance element changes the resistance thereof as a function of a temperature and/or an electromagnetic field. To this end, the resistance element is designed to reduce a temperature rise of the distal end caused by energy absorption from, for example, an electromagnetic field.

21 Claims, 9 Drawing Sheets

APPARATUS FOR MEDICAL APPLICATIONS

CROSS-REFERENCE TO RELATED APPLICATIONS

This patent application claims the benefit of U.S. Provisional Patent Application Ser. No. 61/294,864 entitled "Apparatus for Medical Applications", filed on Jan. 14, 2010, the entire disclosure of which is incorporated by reference herein.

FIELD OF THE INVENTION

The present invention relates to an apparatus for medical applications and, more particularly to, and apparatus for medical applications including an oblong conductive element having a distal end. Such an oblong conductive element can be a lead, for example.

BACKGROUND OF THE INVENTION

Such apparatuses are used, among other things, in an implantable defibrillation system 101, as that known from U.S. Pat. No. 5,531,766, for example, and illustrated in FIG. 1 herein. In order to stimulate the heart H of a patient P, a defibrillator 102 is electrically connected to a lead 103, which in this example carries a special electrode in the form of a shock electrode 104 which is located at the distal end thereof and placed in the patient's heart. Defibrillation typically takes place in a monopolar manner using a current path between this electrode 104 and a counter electrode 105, which is located close to or removed from the heart H to be stimulated. For example, the housing of the defibrillator 102, which accommodates the units for detecting heart signals and for generating electric pulses, may act as a counter electrode 105.

Figure 2:
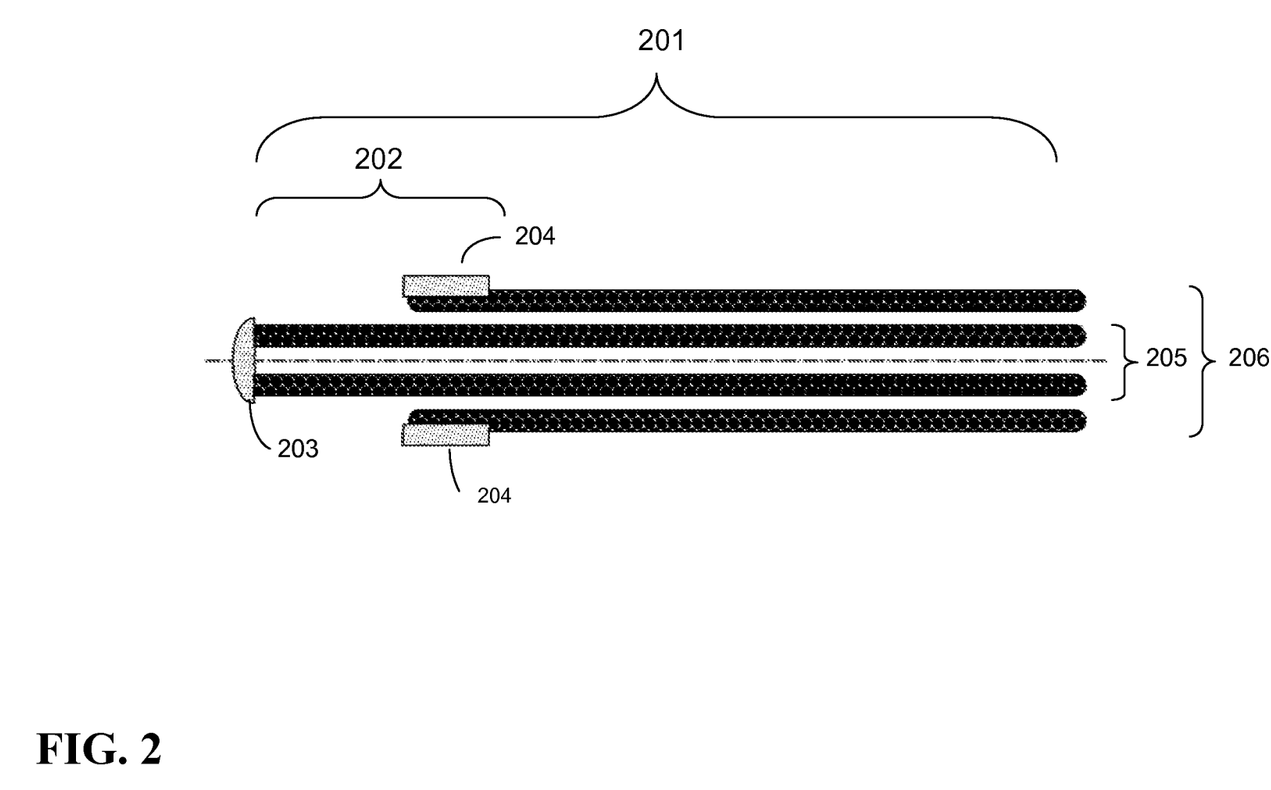
FIG. 2 shows an embodiment of a distal end of a lead.

In another possible embodiment, FIG. 2 shows the distal end of a lead 201. For implementing what is referred to as a bipolar cardio version, the tip 202 of the lead comprises two electrodes 203 and 204. While the electrode 203 forms a contact at the tip of the lead 201, the electrode 204 is designed as an annular contact on the circumference of the lead. The feed lead comprises two helically wound conductors 205 and 206, each of which electrically connects the electrodes 203 and 204 to a connector plug (not shown) at the proximal end of the lead.

Figure 1:
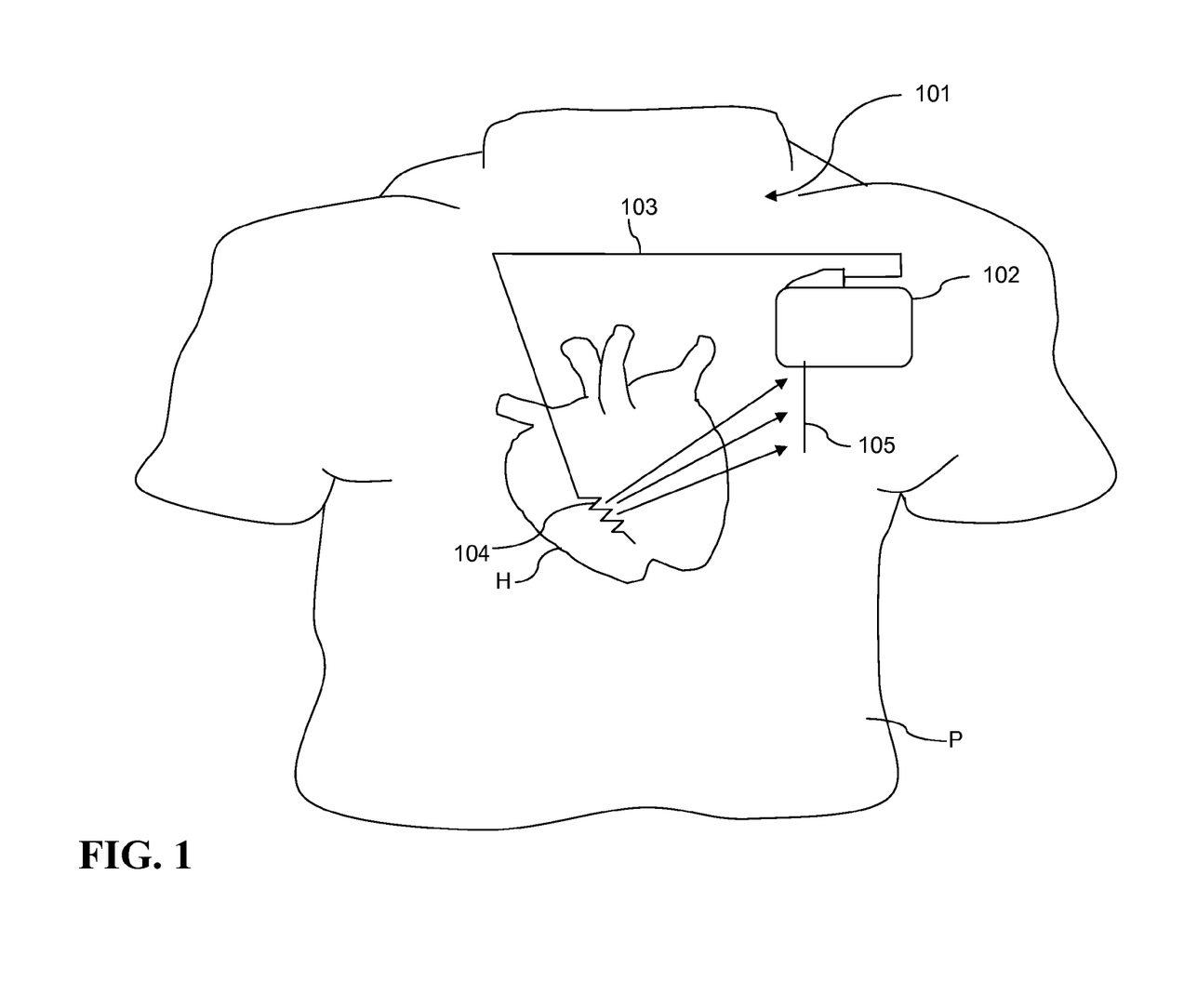
FIG. 1 shows a basic design of an implantable defibrillation system.

At present, patients wearing a conventional defibrillation system according to FIG. 1 cannot undergo magnetic resonance imaging (MRI) examinations, because the strong alternating electromagnetic fields may produce considerable heating of the tip of the lead and resultant damage to the surrounding tissue.

Figure 3:
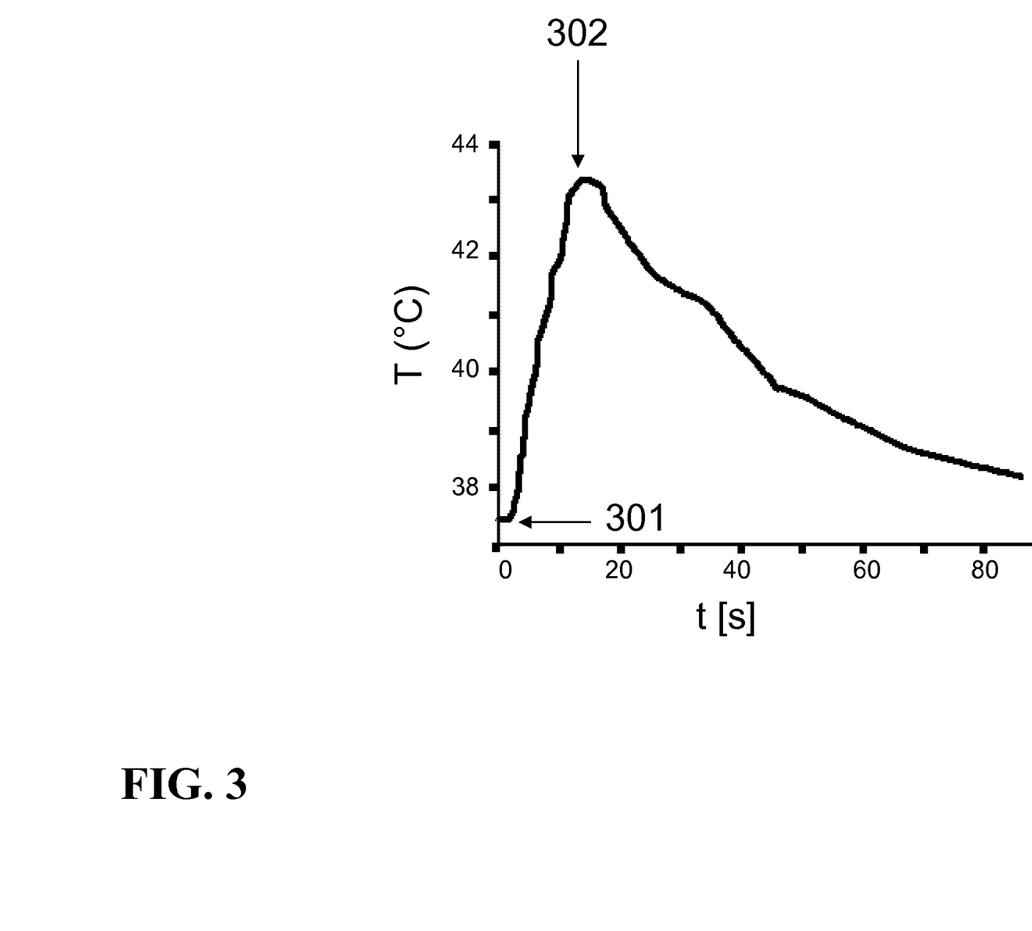
FIG. 3 illustrates a temperature curve of a tip of a lead while coupling an electromagnetic field by way of a magnetic resonance imaging unit.

FIG. 3 illustrates a typical temperature curve of the tip of a lead of a defibrillation system in a magnetic resonance imaging unit. As the electromagnetic field (denoted with 301) is activated, the temperature of the tip of the lead rises rapidly, wherein the degree of the increase and the maximum temperature occurring are highly dependent on the lead position relative to the electromagnetic field of the magnetic resonance imaging unit. When the alternating electromagnetic field (denoted with 302) is deactivated, the tip of the lead cools off relatively quickly due to the comparatively low thermal capacity thereof.

In order to solve the heating problem described above, U.S. Publication No. 2009/0105789 proposes the use of a temperature-dependent switch, which disconnects the tip of the lead from the feed lead upon heating. Such a switch, however, results in disadvantageous design properties of the lead, particularly in rigidity of the electrode. Furthermore, the thermal switch exhibits considerable hysteresis, the temperature range is difficult to set, and the tip of the lead can only be completely connected or disconnected, whereby in the disconnected state no stimulation of the heart or conductance of signals is possible.

The problem of the electrode surfaces overheating also occurs with the temporary use of electrodes, electrically active catheters, and metal, partially insulated guide wires in the MRI unit. The application of the MRI unit, for example as part of electrophysiological examinations (mapping), is therefore limited accordingly.

The present invention is directed toward overcoming one or more of the above-identified problems.

SUMMARY OF THE INVENTION

According to one concept of the invention, an apparatus for medical applications is provided, which includes an oblong conductive element having a distal end, wherein in the vicinity of the distal end a resistance element is disposed, which varies the resistance thereof as a function of a temperature and/or an electromagnetic field. The resistance element is designed to reduce a temperature rise of the distal end caused by energy absorption from an electromagnetic field.

To this end, the resistance element may be a temperature-dependent resistor, the operating point of which ranges between 38° C. and 45° C., for example. Furthermore, the resistance element may be a magnetic field-dependent resistor, such as a giant magnetoresistance ("GMR") element. Field effect transistors may also be used to produce a circuit that provides variable resistance.

In one embodiment, the resistance element is disposed no more than 20 mm away from a tip of the oblong conductive element. The resistance element may be disposed such that good thermal conductivity exists between the tip and the resistance element, in particular the resistance element can connect directly to the tip. In one embodiment, the resistance element is disposed between the tip and a feed lead.

In one embodiment, the resistance element is a PTC thermistor, which is designed such that it has low resistance at body temperature and high resistance at a temperature above the body temperature, but below a temperature that damages tissue. When coupling an electromagnetic field by way of the magnetic resonance imaging unit, the distal end by way of the PTC thermistor has a high-resistance connection to the proximal end of the oblong conductive element such that the temperature rise of the distal end decreases considerably. In one embodiment, the PTC thermistor is designed such that it has low resistance at 37° C. and high resistance at 44° C.

The distal end may enclose the PTC thermistor at least partially. The distal end may be coated.

In one embodiment, the resistance element has the shape of a cylinder with a concentric bore, wherein the cylinder at least partially forms the oblong conductive element or surrounds it.

The oblong conductive element may include a dissipating unit, which is disposed in the vicinity of the distal end and conducts the energy absorbed from an electromagnetic field away from the distal end. By dissipating the energy, the maximum temperature at the distal end can be further reduced.

In one embodiment, the dissipating unit includes an NTC thermistor, which is designed such that it has high resistance at body temperature and low resistance at a temperature above the body temperature, but below a temperature that damages tissue. In one embodiment, the NTC thermistor is designed such that it has high resistance at 37° C. and low resistance at 44° C., however, values that deviate from these are also possible, and the invention is not limited thereby.

In one embodiment, the distal end includes an electrode pole. The oblong conductive element may include at least one further electrode pole. In this configuration, the apparatus according to the invention can be equipped to ensure optimal distribution of the energy from the oblong conductive element to the electrode poles to the extent possible.

In one embodiment, the apparatus according to the invention is designed as an electrode lead. The apparatus may include an electrode disposed at a distance from the distal end, in particular an annular electrode or a shock coil of a multipolar electrode, to which in particular the dissipating unit dissipates the energy absorbed. The distal end can be an electrode for stimulating a heart, an ICD (implantable cardioverter defibrillator) electrode, a transvenous ICD electrode, a subcutaneously implantable ICD electrode, or an electrode for neurostimulation.

Using the apparatus according to the invention, for example, an MRI-safe electrode lead can be provided in a simple and inexpensive manner. The lead remains flexible. In addition, when using the apparatus according to the invention in a defibrillator in an MRI environment it is possible to provide effective stimulation such that also patients dependent on pacemakers can be supplied during an examination in an MRI unit.

The apparatus according to the invention can be configured as a catheter, in particular an ablation, balloon or insertion catheter, as a guide wire, as an introducer sheath or a stent.

The invention further encompasses an implant (a system) having an apparatus according to the invention, wherein the distal end includes an electrode for stimulating a body part and the electrode is controlled based on a stimulation parameter. To this end, the implant includes a device for detecting a change in the resistance of the resistance element and a device for adapting the stimulation parameter based on the detected change in the resistance of the resistance element. The implant may in particular include an input stage having a sensor for receiving measurement signals, which describe the state of the body part to be stimulated, and a device for adapting a characteristic of the input stage based on the detected change in the resistance of the resistance element.

In this way, when a patient with a defibrillator is located in a magnetic resonance imaging unit, the stimulation power of the defibrillator, for example, can be adapted to the situation. Furthermore, for example, the sensitivity of a measurement unit used by the defibrillator for controlling the stimulation behavior thereof can be adapted.

BRIEF DESCRIPTION OF THE DRAWINGS

Additional details of the invention and corresponding embodiments are described below with reference to the figures.

DETAILED DESCRIPTION OF THE INVENTION

Figure 4:
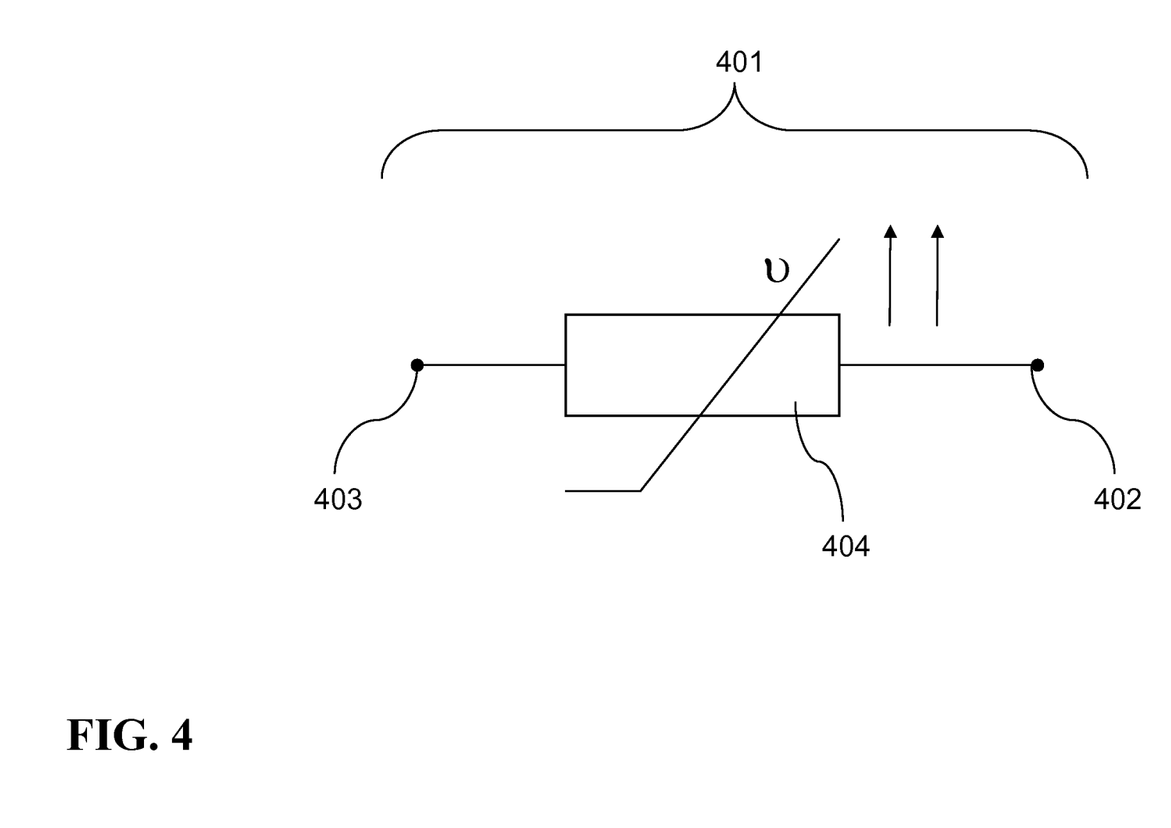
FIG. 4 shows an equivalent circuit of an embodiment of an apparatus according to the invention.

FIG. 4 shows an equivalent circuit of an apparatus 401 according to the invention, which is designed as an electrode lead. An oblong conductive element 402 includes a distal end 403 and a PTC thermistor 404. As the distal end 403 heats when an alternating electromagnetic field is coupled by, for example, an MRI unit, the PTC thermistor 404 located in the vicinity of the distal end is heated. As a result, the PTC thermistor 404 has high resistance and thereby reduces the temperature rise.

Figure 5:
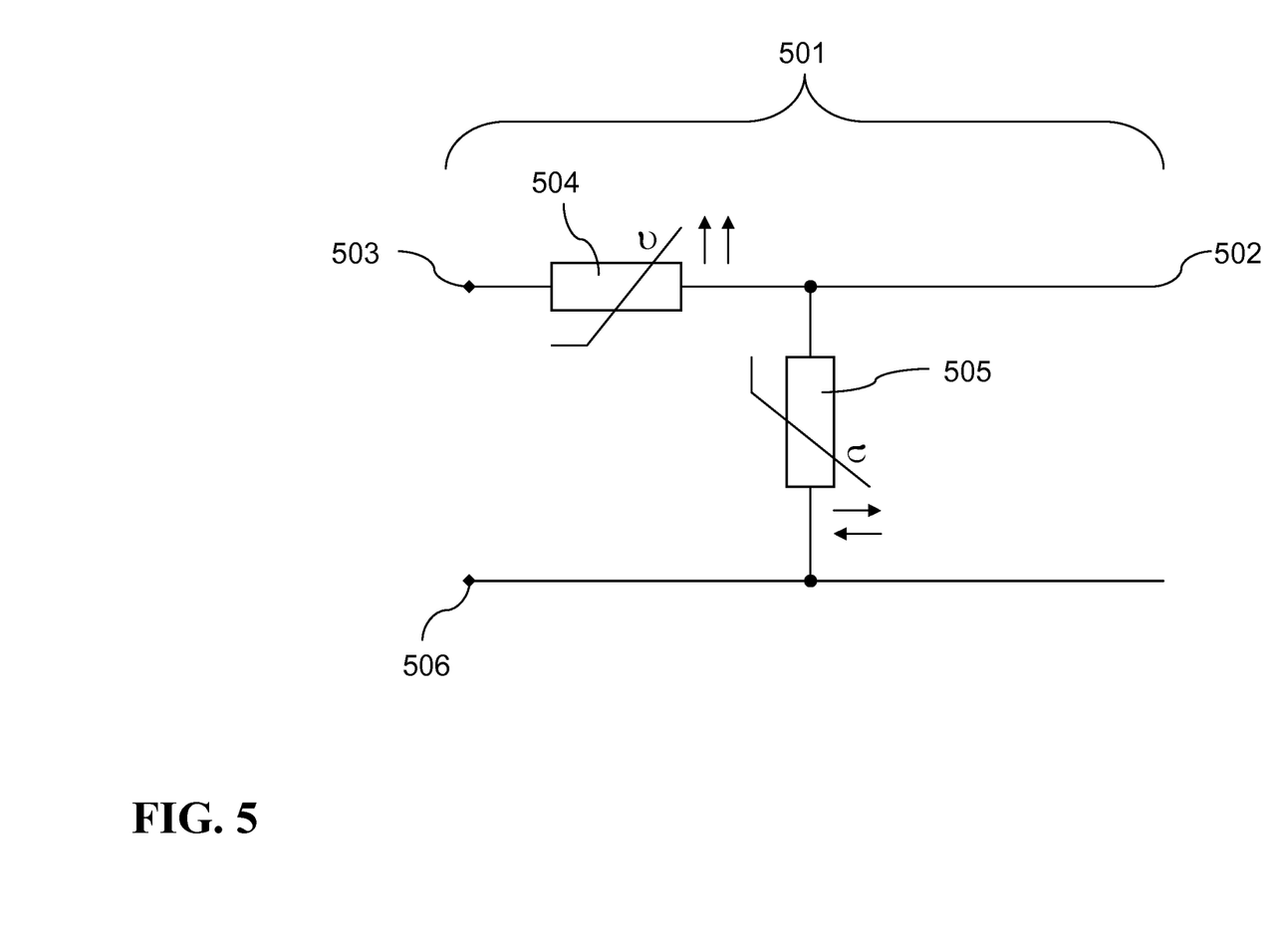
FIG. 5 shows an equivalent circuit of a further embodiment of an apparatus according to the invention.

FIG. 5 shows an equivalent circuit of a further embodiment of an apparatus 501 according to the invention. An oblong conductive element 502 includes a distal end 503 and a PTC thermistor 504. The oblong conductive element 502 furthermore includes an NTC thermistor 505. The thermal resistor 505 connects the oblong conductive element 502 to an annular electrode 506. As the temperature rises, the NTC thermistor 505 has low resistance and thereby dissipates the energy absorbed from the electromagnetic field from the distal end 503 to the thermally less critical annular electrode 506.

Figure 6:
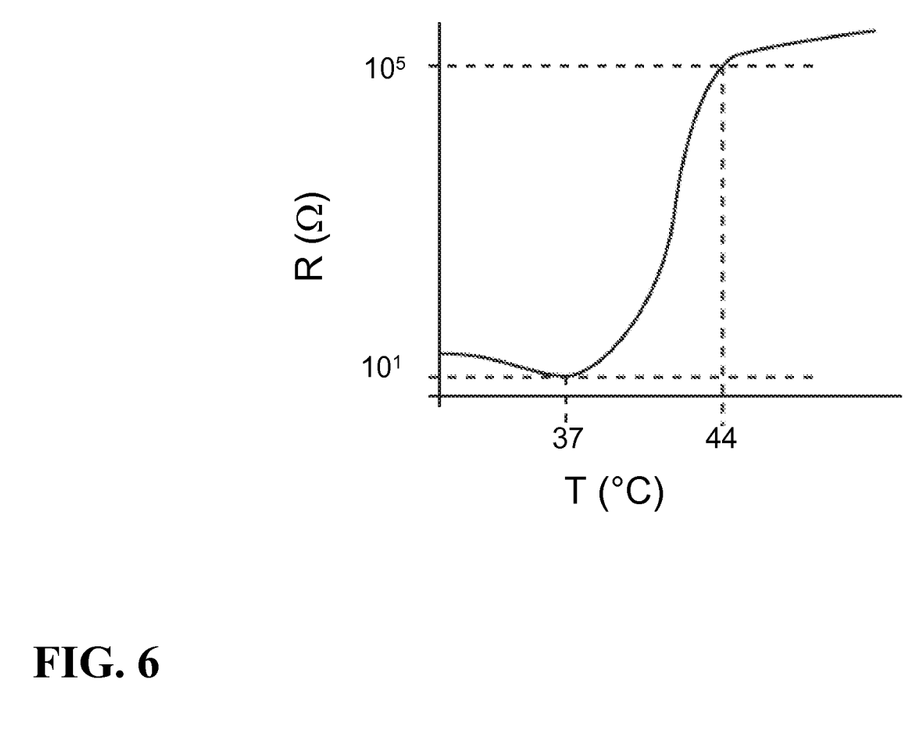
FIG. 6 shows an example of a resistance curve of a PTC thermistor.

FIG. 6 illustrates a possible resistance curve of the PTC thermistors 404, 504 shown in FIGS. 4 and 5. In the example shown, the lowest resistance value of the PTC thermistor is at 37° C. As the temperature rises, the resistance of the PTC thermistor increases and reaches a high-resistance value below the threshold of tissue damage, but clearly above the potential core body temperature, including fever. An accordingly reverse characteristic applies to the NTC thermistor 505 shown in FIG. 5.

Figure 7:
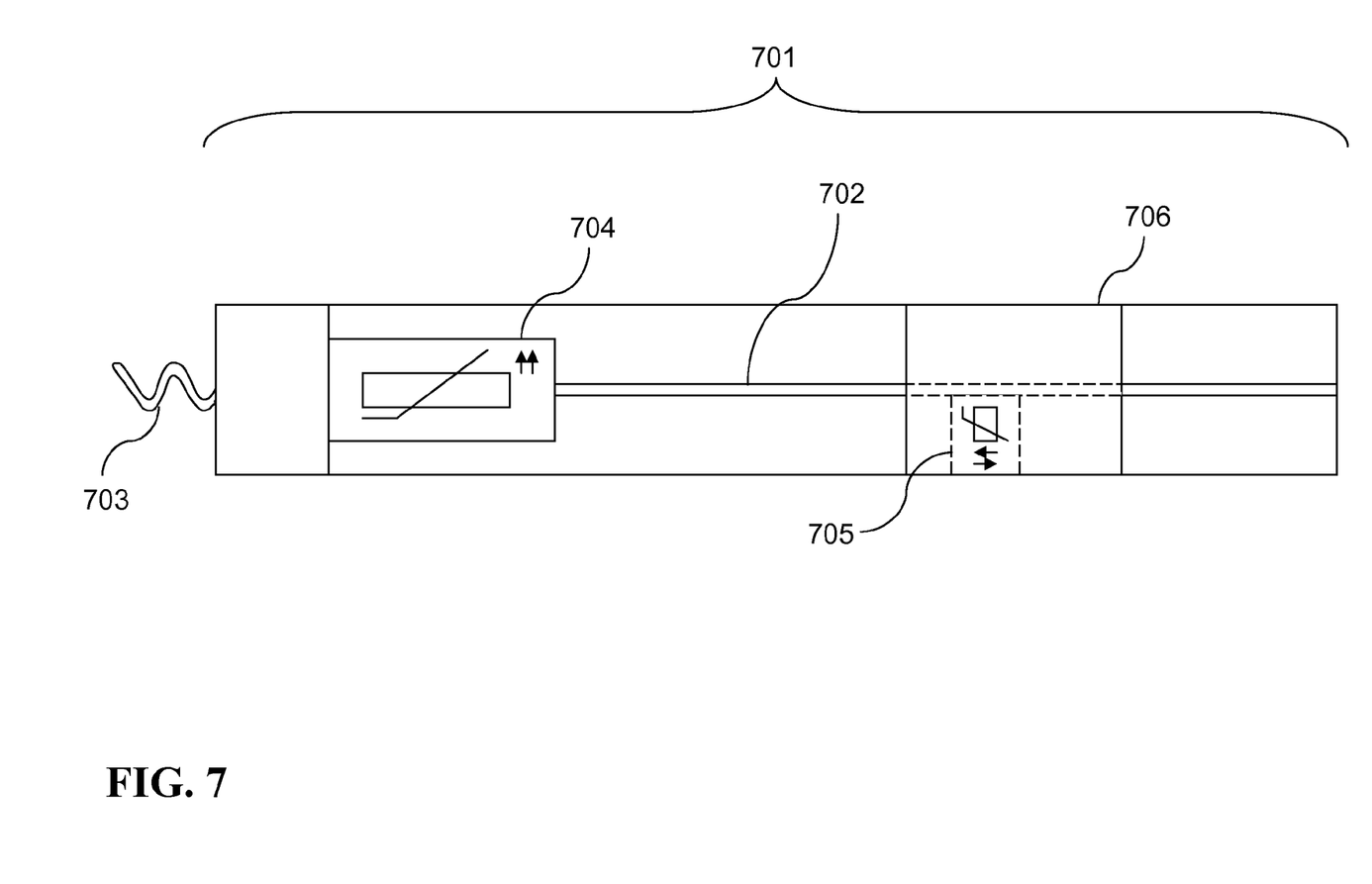
FIG. 7 shows an embodiment of an apparatus according to the invention.

FIG. 7 shows an embodiment of an apparatus according to the invention, which is designed as an electrode lead 701. A distal end 703 of the oblong conductive element 702 is designed as a screw and connected by the oblong conductive element 702 to a connector plug, which is not shown. According to the invention, a cylindrical PTC thermistor 704 is mounted in the vicinity of the distal end 703, said PTC thermistor being connected to the oblong conductive element 702. An NTC thermistor 705 is located between the oblong conductive element 702 and an annular electrode 706.

Figure 8:
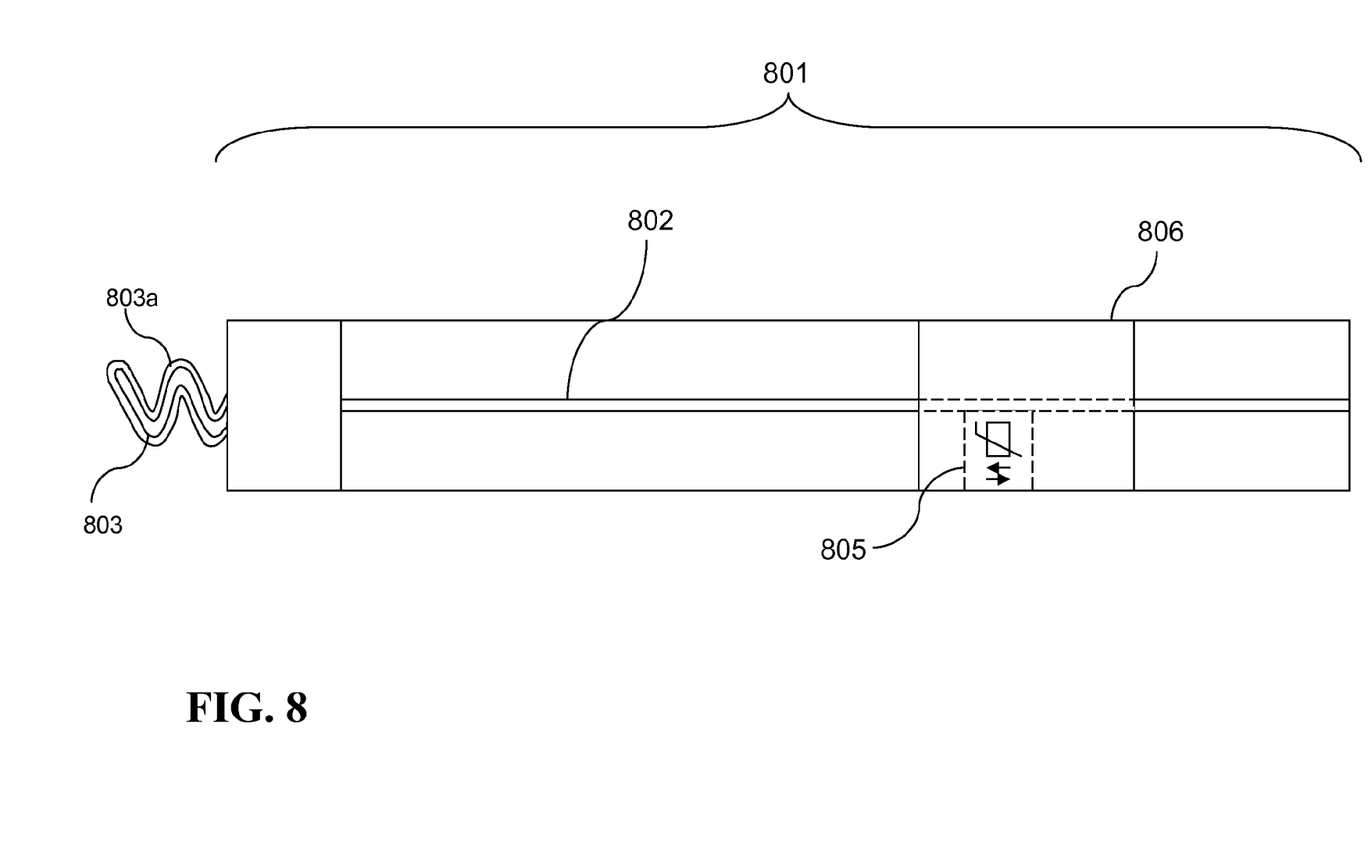
FIG. 8 shows a further embodiment of an apparatus according to the invention.

FIG. 8 describes a further embodiment of an apparatus according to the invention, which is designed as an electrode lead 801. An oblong conductive element 802, an NTC thermistor 805, and an annular electrode 806 correspond to the oblong conductive element 702 and the annular electrode 706 from FIG. 7. Deviating from the embodiment in FIG. 7, in FIG. 8 a distal end 803 is made of a PTC thermistor material, such as a sintered body made of barium nitrate, thereby allowing a separate PTC thermistor to be foregone. To this end, the distal end 803 is covered with a coating 803a.

Figure 9:
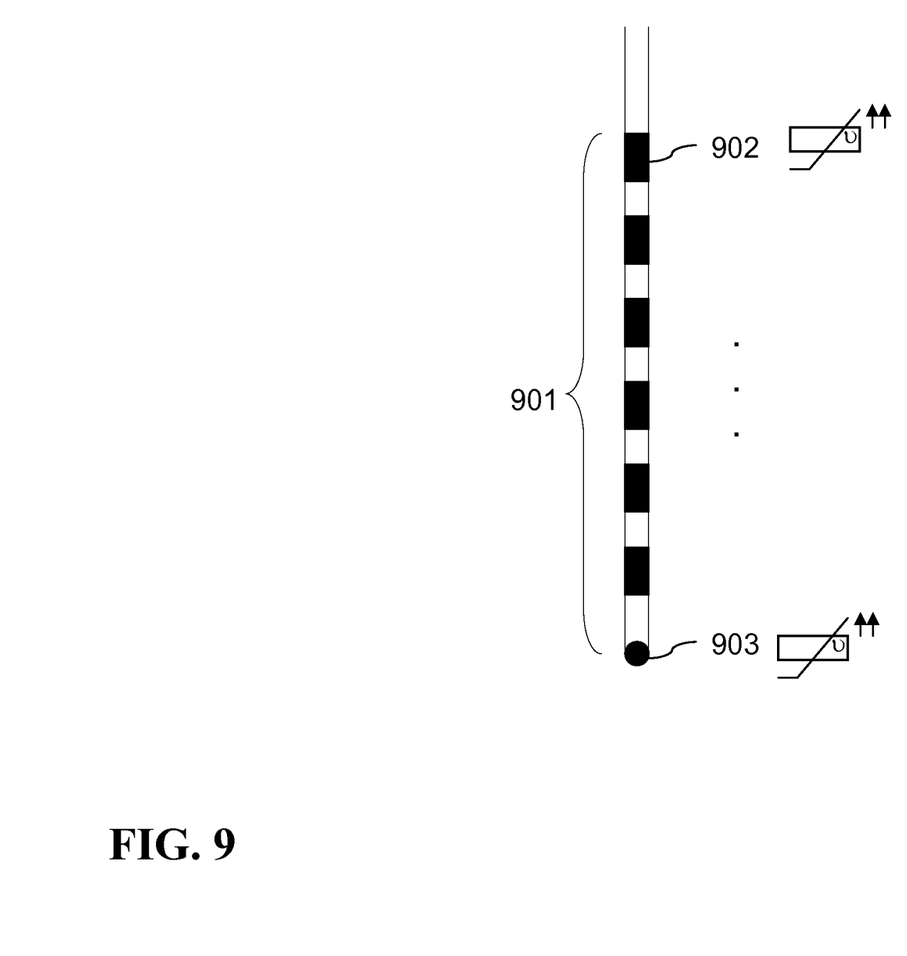
FIG. 9 shows a further embodiment of an apparatus according to the invention.

FIG. 9 describes a further embodiment of an apparatus according to the invention, which is designed as a multipolar electrophysiological mapping catheter 901. Each of the annular electrodes 902 and the tip electrode 903 are produced from a PTC thermistor material or include the same. Due to the identical electrode surfaces, each of the annular and/or tip electrode has the same likelihood of heating in the critical range such that none of the electrodes mentioned can be connected as counter electrodes to an NTC thermistor.

In a further embodiment of the invention, a balloon catheter includes what is referred to as a hypotube shaft, which provides reinforcement for guiding the catheter, and is made of a galvanically conductive material and extends from the proximal end to approximately 40 cm in front of the balloon. According to the invention, the hypotube shaft is designed as an apparatus according to the invention so as to reduce heating in an MRI unit.

According to the invention, additionally ablation catheters and introducer sheaths, which include electrodes at the distal end and are connected to the proximal end by way of an electrical feed lead, may be designed as an apparatus according to the invention.

The implementation of the invention is not limited to the examples described above and concepts emphasized, but is likewise possible in a plurality of modifications, which are within the scope of standard practice in the art. The present invention is not confined to the specific details set forth, but includes various changes and modifications that may suggest themselves to those skilled in the art, all falling within the spirit and scope of the present invention as defined by the following claims, which are to be given their full scope and breadth.

It will be apparent to those skilled in the art that numerous modifications and variations of the described examples and embodiments are possible in light of the above teachings of the disclosure. The disclosed examples and embodiments are presented for purposes of illustration only. Therefore, it is the intent to cover all such modifications and alternate embodiments as may come within the true scope of this invention, which is to be given the full breadth thereof. Additionally, the disclosure of a range of values is a disclosure of every numerical value within that range.

We claim:

1. An apparatus for medical applications, comprising:
an oblong conductive element having a distal end and a resistance element that is disposed in the vicinity of the distal end and electrically connected to the distal end and changes the resistance thereof as a function of a temperature and/or an electromagnetic field, wherein the resistance element is designed to reduce a temperature rise of the distal end, the rise caused by energy absorption at the distal end from an electromagnetic field.

2. The apparatus according to claim 1, wherein the resistance element includes a PTC thermistor, which is designed such that it has a low resistance at body temperature and a high resistance at a temperature above the body temperature, but below a temperature that damages body tissue.

3. The apparatus according to claim 2, wherein the distal end encloses the PTC thermistor at least partially.

4. The apparatus according to claim 1, wherein the resistance element has the shape of a cylinder with a concentric bore, the cylinder at least partially forming the oblong conductive element or surrounding it.

5. The apparatus according to claim 1, wherein the oblong conductive element comprises a dissipating unit, which is disposed in the vicinity of the distal end and electrically connected to the resistance element and conducts the energy absorbed from an electromagnetic field away from the distal end.

6. The apparatus according to claim 5, wherein the dissipating unit comprises an NTC thermistor, which is designed such that it has a low resistance at body temperature and a high resistance at a temperature above the body temperature, but below a temperature that damages body tissue.

7. The apparatus according to claim 1, wherein the apparatus is designed as a catheter, said catheter including an ablation, balloon or insertion catheter.

8. The apparatus according to claim 1, wherein the apparatus is designed as a guide wire.

9. The apparatus according to claim 1, wherein the apparatus is designed as an introducer sheath.

10. The apparatus according to claim 1, wherein the apparatus is designed as a stent.

11. An electrode lead for medical applications, comprising:
an oblong conductive element having a distal end and a resistance element that is disposed in the vicinity of the distal end and electrically connected to the distal end and changes the resistance thereof as a function of a temperature and/or an electromagnetic field, wherein the resistance element is designed to reduce a temperature rise of the distal end, the rise caused by energy absorption at the distal end from an electromagnetic field.

12. The electrode lead according to claim 11, further comprising an electrode disposed at a distance from the distal end to which a dissipating unit dissipates the energy absorbed, wherein the electrode includes an annular electrode or a shock coil of a multipolar electrode.

13. The electrode lead according to claim 11, wherein the distal end comprises an electrode for stimulating a heart, an ICD electrode, a transvenous ICD electrode, a subcutaneously implantable ICD electrode, or an electrode for neurostimulation.

14. An implant comprising an electrode lead according to claim 11, wherein the distal end comprises an electrode for stimulating a body part, wherein the electrode is controlled based on a stimulation parameter, and wherein the implant further comprises a device for detecting a change in the resistance of the resistance element and a device for adapting the stimulation parameter based on the detected change in the resistance of the resistance element.

15. The electrode lead according to claim 11, wherein the resistance element includes a PTC thermistor, which is designed such that it has a low resistance at body temperature and a high resistance at a temperature above the body temperature, but below a temperature that damages body tissue.

16. The electrode lead according to claim 15, wherein the distal end encloses the PTC thermistor at least partially.

17. The electrode lead according to claim 11, wherein the resistance element has the shape of a cylinder with a concentric bore, the cylinder at least partially forming the oblong conductive element or surrounding it.

18. The electrode lead according to claim 11, wherein the oblong conductive element comprises a dissipating unit, which is disposed in the vicinity of the distal end and electrically connected to the resistance element and conducts the energy absorbed from an electromagnetic field away from the distal end.

19. The electrode lead according to claim 18, wherein the dissipating unit comprises an NTC thermistor, which is designed such that it has a low resistance at body temperature and a high resistance at a temperature above the body temperature, but below a temperature that damages body tissue.

20. An apparatus for medical applications, comprising:
an oblong conductive element having a distal end and a resistance element that is disposed in the vicinity of the distal end and changes the resistance thereof as a function of a temperature and/or an electromagnetic field, wherein the resistance element is designed to reduce a temperature rise of the distal end, the rise caused by energy absorption from an electromagnetic field,
wherein the distal end comprises an electrode for stimulating a body part, wherein the electrode is controlled based on a stimulation parameter, and wherein the implant further comprises a device for detecting a change in the resistance of the resistance element and a device for adapting the stimulation parameter based on the detected change in the resistance of the resistance element, and wherein the implant further comprises an input stage having a sensor for receiving measurement signals, which describe the state of the body part to be stimulated, and a device for adapting a characteristic of the input stage based on the detected change in the resistance of the resistance element.

21. An electrode lead for medical applications, comprising:
an oblong conductive element having a distal end and a resistance element that is disposed in the vicinity of the distal end and changes the resistance thereof as a function of a temperature and/or an electromagnetic field, wherein the resistance element is designed to reduce a temperature rise of the distal end, the rise caused by energy absorption from an electromagnetic field, wherein the distal end comprises an electrode for stimulating a body part, wherein the electrode is controlled based on a stimulation parameter, and wherein the implant further comprises a device for detecting a change in the resistance of the resistance element and a device for adapting the stimulation parameter based on the detected change in the resistance of the resistance element, and wherein the implant further comprises an input stage having a sensor for receiving measurement signals, which describe the state of the body part to be stimulated, and a device for adapting a characteristic of the input stage based on the detected change in the resistance of the resistance element.

\* \* \* \* \*